(12) United States Patent
Zhou et al.

(10) Patent No.: US 7,258,773 B2
(45) Date of Patent: Aug. 21, 2007

(54) SOLID POLYMER ELECTROLYTE OXYGEN SENSOR

(75) Inventors: Huafang Zhou, Sunnyvale, CA (US);
Hong T. Sun, Los Gatos, CA (US);
Peter C. Hsi, Fremont, CA (US)

(73) Assignee: RAE Systems, Inc., San Jose, CA (US)

( * ) Notice: Subject to any disclaimer, the term of this patent is extended or adjusted under 35 U.S.C. 154(b) by 828 days.

(21) Appl. No.: 10/640,125

(22) Filed: Aug. 12, 2003

(65) Prior Publication Data

US 2005/0034987 A1    Feb. 17, 2005

(51) Int. Cl.
*G01N 27/407*    (2006.01)
*G01N 27/409*    (2006.01)

(52) U.S. Cl. ...................... 204/431; 204/426
(58) Field of Classification Search ............... 204/431, 204/432, 424, 426
See application file for complete search history.

(56) References Cited

U.S. PATENT DOCUMENTS

| | | | |
|---|---|---|---|
| 4,227,984 A | 10/1980 | Dempsey et al. | |
| 4,632,746 A | 12/1986 | Bergman | |
| 5,164,053 A * | 11/1992 | Razaq et al. ............ | 205/784 |
| 5,573,648 A | 11/1996 | Shen et al. | |
| 5,650,054 A | 7/1997 | Shen et al. | |
| 6,068,748 A | 5/2000 | Berger et al. | |
| 6,080,294 A | 6/2000 | Shen et al. | |
| 6,179,986 B1 | 1/2001 | Swette et al. | |
| 6,200,443 B1 | 3/2001 | Shen et al. | |
| 6,827,769 B2 * | 12/2004 | Auslander et al. ....... | 106/31.32 |

FOREIGN PATENT DOCUMENTS

| | | |
|---|---|---|
| EP | 0762117 A2 | 3/1997 |
| EP | 0974834 A2 * | 1/2000 |

OTHER PUBLICATIONS

McLaughlin, Glen W. et al., "Microfabricated Solid-state Dissolved Oxygen Sensor" Elsevier, Sensors and Actuators B 83 (2002) 138-148.
Wallgren, Kirsi et al., "Oxygen Sensors Based on a New Design Concept for Amperometric Solid State Devices" Elsevier, Sensors and Actuators B 60 (1999) 174-183.

* cited by examiner

*Primary Examiner*—Alex Noguerola
(74) *Attorney, Agent, or Firm*—David T. Millers (57) ABSTRACT

An oxygen sensor includes a solid polymer electrolyte, e.g., on an acid treated Nafion membrane and uses a diffusion-limited fuel cell type reactions. The sensor avoids electrolyte leakage and avoids consumption of electrodes. In different configurations, a counter or reference electrode can be on the same or the opposite side of the electrolyte as a sensing electrode. An insert limits and controls oxygen diffusion into a sensing chamber containing the sensing electrode that catalyzes reduction of oxygen. Applying appropriate bias voltages to the reference and sensing electrodes causes an output current of the sensing electrode to be proportional to the rate of oxygen consumption based on Frick's law under a diffusion-limited mode. The output current can be measured, e.g., using a resistor to convert the current to a voltage signal.

54 Claims, 4 Drawing Sheets

SOLID POLYMER ELECTROLYTE OXYGEN SENSOR

BACKGROUND

Solid electrolyte oxygen sensors and galvanic cell oxygen sensors are currently the most widely used sensors for monitoring gaseous oxygen. Solid electrolyte oxygen sensors typically include an electrolyte body made of an oxygen-ion-conductive ceramic such as zirconium ($ZrO_2$) doped with traces of metal oxides (e.g., $Y_2O_3$). Porous electrodes on opposite faces of the body permit the diffusion of oxygen ions through the electrolyte body. Thus, when one electrode is exposed to a reference gas (e.g., air) and the other electrode is exposed to a sample gas (e.g., engine exhaust), a difference in oxygen partial pressure at the electrodes causes diffusion of oxygen ions that results in a corresponding voltage difference between the electrodes. A limitation of these solid electrolyte oxygen sensors is that the ceramic electrolytes used in the sensors only conduct oxygen ions when heated to temperatures above 400 to 600° C. Accordingly, the solid electrolyte sensors generally require time to heat up before becoming responsive, and an auxiliary electrical heater may be needed in the sensor as described in U.S. Pat. No. 4,175,019 to Michael P. Murphy.

Galvanic cell oxygen sensors using liquid electrolytes are generally simple, cheap, and operable at room temperature. U.S. Pat. Nos. 4,132,616 and 4,324,632 to Tantram et al., U.S. Pat. No. 4,495,051 to Fujita et al., U.S. Pat. No. 4,775,456 to Shah et al., U.S. Pat. No. 4,988,428 to Matthiessen et al., and U.S. Pat. No. 5,284,566 to Cuomo et al. describe some configurations for known galvanic cell oxygen sensors. Galvanic cell oxygen sensors operate on the same principle as a battery and generally include a cathode and an anode in contact with a liquid electrolyte. The cathode is typically made of a metal such as platinum, gold, or silver that is an effective catalyst for the electrolytic reduction of oxygen, and the anode is generally made of lead. The reduction of oxygen at the cathode produces oxygen ions that flow through the electrolyte to the anode and react with the lead anode. The resulting current between the cathode and anode is linearly proportional to the oxygen concentration, so that oxygen concentration measurements are easily determined from measurements of the current between the anode and cathode.

Galvanic cell sensors have several significant disadvantages. In particular, their life expectancy is a function of usage and the resulting anode consumption. Leakage of liquid electrolyte can also reduce sensor life and damage surrounding components. Furthermore, galvanic cell sensors have a tendency to read low due to loss in sensitivity as the sensors age. For most process control applications, false low oxygen readings can produce dire consequences. As a result, galvanic cell sensors must be frequently recalibrated, sometimes as often as once per day, depending on the criticality of the application. Another major drawback of galvanic cell sensors is their susceptibility to oxygen shock that results when galvanic cell sensors are exposed to a high concentration of oxygen. The high oxygen concentration can cause local variations of electrolyte composition that may take hours to equalize.

Polymer electrolytes have found applications in many areas of electrochemical technology. Nafion, for example, is a solid polymer electrolyte that has been widely used in the development of sensors and fuel cells. Nafion has an excellent ionic conductivity, outstanding chemical and thermal stability, and good mechanical strength. Additionally, Nafion, modified with a variety of noble metals, can create composite materials with ionic and electronic conductivity characteristics that are desirable for gas sensing. Galvanic cell sensors based on the solid polymer electrolyte (SPE) have been used to detect carbon monoxide (CO) and toxic gas with good performance as described in U.S. Pat. No. 4,227,984 to Dempsey et al. and U.S. Pat. Nos. 5,573,648, 5,650,054, 6,179,986, and 6,200,443B1 to Shen et al.

U.S. Pat. No. 4,227,984 to Dempsey et al. describes a gas sensor using three electrodes on the surface of a solid polymer electrolyte mounting membrane to detect toxic gas such as carbon monoxide (CO) or nitrogen dioxide ($NO_2$). U.S. Pat. Nos. 5,573,648, 5,650,054, 6,179,986, and 6,200,443 B1 describe an SPE gas sensor with a two-electrode or three-electrode system for measuring carbon monoxide and other toxic gases in the environment. These toxic gas sensors generally are low cost and accurate and have a long useful life but have not been suitable for oxygen detection.

U.S. Pat. No. 6,080,294 to Shen et al. discloses a galvanic oxygen sensor including a solid polymer electrolyte and liquid electrolyte electrically connected in series between a cathode and an anode. This sensor is similar to the traditional galvanic cell oxygen sensor but uses the solid polymer electrolyte to control the rate of the electrochemical reaction. This can improve the useful life of the sensor, but the sensor still has many of the same problems as the more conventional galvanic cell oxygen sensors. In particular, using the liquid electrolyte still presents leakage problems. Another drawback is that a permeable membrane that controls oxygen diffusion can introduce larger temperature effects. Further, the lead (Pb) anode is consumed over time, changing the available surface area of the lead anode as lead (Pb) is converted to lead oxide (PbO and $PbO_2$). As a result, the electrochemical activity and current output eventually falls to zero, at which point the sensor must be rebuilt or replaced, causing a lead pollution problem.

Another problem in galvanic oxygen sensors is the use of an alkaline electrolyte, which can be affected by prolonged exposure to acidic gases such as $CO_2$. Most of these sensors should not be used continuously in atmospheres containing more than 25% $CO_2$. In some cases, prolonged exposure to acid gas damages the basic sensor electrolyte. In other situations, high concentrations of acid gas produce a current flux that alters the normal expected output of the sensor at a given concentration of oxygen.

In view of the current state of sensor technology, an easily manufactured oxygen sensor having a long operational lifespan, fast response, low cost, no leakage, and a compact size would be highly desirable.

SUMMARY

In accordance with an aspect of the invention, an oxygen sensor uses fuel cell type reactions and a solid polymer electrolyte to sense or measure oxygen in a sample gas. In comparison to other electrochemical oxygen sensors, the oxygen sensor has a relatively low resistance, a fast response, and a long operating life, without requiring liquid electrolytes, lead electrodes, or consumed parts. The sensor is also operable at room temperature.

In operation of an oxygen sensor in accordance with an exemplary embodiment of the invention, a sensing electrode catalyzes a reaction in which oxygen captures the electrons and combines with hydrogen ions from the solid polymer electrolyte to form water. To compensate for the loss of electrons at the sensing electrode and hydrogen ions in the polymer solid electrolyte, a counter electrode is biased to a voltage that cause electrolysis of water, producing the hydrogen ions and offering electrons. A reference electrode attached to the solid polymer electrolyte can provide a reference voltage relative to the counter and sensing electrode. The electrons from the counter electrode form an output current that flows to the sensing electrode. The resulting current of electrons depends on the rate of oxygen consumption at the sensing electrode and can be measured to determine the oxygen concentration at the sensing electrode. The hydrogen ions created at the counter electrode move to the sensing electrode through the polymer electrolyte, which is a good protonic and electronic conductor.

An important advantage of this type of sensor is that the sensor does not consume electrodes or other materials when sensing oxygen, unlike Galvanic cell sensors that typically consume a lead electrode when detecting oxygen. Moisture required for and generated by the sensor can be introduced through the humidity in the gas being measured and is recycled and preserved in the solid electrolyte and in an optional sealed reservoir. The sensor is thus capable of an operational lifespan of over two years even when used in dry conditions.

One exemplary embodiment of the invention is a gas sensor including a reference electrode, a counter electrode, and a sensing electrode in electrical contact with a block or membrane of a solid electrolyte. A suitable biasing of the sensing electrode relative to the reference electrode permits a reaction of oxygen with the hydrogen ions at the sensing electrode to produce water and in the process draws electrons through the sensing electrode. To supply the electrons to the sensing electrode and hydrogen ions in the polymer electrolyte, the counter electrode can be biased for the electrolysis of water to release hydrogen ions and electrons. The hydrogen ions enter the polymer electrolyte, and the electrons flow to the sensing electrode. The resulting current through the sensing electrode from the counter electrode indicates a measured oxygen concentration.

The sensor can further include an insert or restriction between the sensing electrode and a source of a gas being measured. The insert includes a capillary pore or some other diffusion barrier that controls a flow of oxygen to the sensing electrode. With the diffusion barrier, the diffusion rate limits the reaction at the sensing electrode, so that the reaction rate and the output signal are proportional to the oxygen content of the gas outside the sensor.

A housing of the detector can include a reservoir that contains water that maintains humidity in or around the solid electrolyte. In the reservoir, a moisture-retaining agent such as a polymer material containing $H_2SO_4$ can maintain a suitable moisture level in the solid electrolyte for a long useful lifetime of the oxygen detector.

The solid electrolyte is generally a protonic conductive electrolyte membrane. The solid electrolyte can be a perfluorinated ion-exchange polymer such as Nafion or a protonic conductive polymer such as poly(ethylene glycol), poly (ethylene oxide), poly(propylene carbonate). When used, a Nafion membrane can optionally be treated with an acid such as $H_3PO_4$, which improves the moisture retention characteristics of Nafion and the conductivity of hydrogen ions through the Nafion membrane. The sensing, counter and reference electrodes can be hot-pressed onto the Nafion membrane to provide a high conductivity between the electrodes and the solid electrolyte.

The electrodes and particularly the sensing electrode are preferably made of a porous conductive material. The sensing and counter electrodes are preferably made of a material that catalyses oxygen reduction and may include platinum, gold, ruthenium, palladium, iridium, platinum/ruthenium, platinum/iridium, platinum/palladium alloy, carbon, and platinum/carbon. The reference electrode can contain a noble metal such as platinum and gold or a high conductivity metal/salt combination such as Ag/AgCl.

The sensing electrode is on a side of the solid electrolyte that is exposed to the gas being measured. However, in various alternative embodiments of the invention, either the counter electrode or the reference electrode can be on the same side as the sensing electrode or on the side opposite to the sensing electrode. Additionally, the shapes of the sensing, counter, and reference electrodes can vary. In one embodiment, all of the electrodes are circular. In another embodiment of the invention, the sensing electrode and the counter electrode include a disk and a concentric ring surrounding the disk.

Another embodiment of the invention is a miniature or button-type solid polymer. Generally, very small sensors for sensing oxygen have not been possible because common galvanic oxygen sensors need an anode containing a lot of lead for consumption. Galvanic sensors thus could not be reduced to button size (e.g., about 1 $cm^3$ or less). However, an oxygen sensor using a solid polymer as a support electrolyte and a fuel cell reaction for sensing can be made quite compact.

One button-type oxygen sensor in accordance with and embodiment of the invention includes a first electrode as sensing electrode, a solid polymer as support electrolyte, and a second electrode as a counter/reference electrode. A gas permeation membrane, which can be made of polypropylene and polyester, replaces the diffusion pore to control the oxygen diffusion rate. Pieces of glass fiber, which permeated with $H_2SO_4$, can be used to adjust humidity. The basic operating principles the button-type oxygen sensor is the same as those of a larger fuel cell oxygen sensor, but the second electrode in the button-type oxygen sensor functions as a counter electrode to balance the reaction at a sensing electrode by providing hydrogen ions and electrons and as a reference electrode for measuring a relative bias to the sensing electrode. The gas permeable membrane that limits oxygen diffusion to a sensing electrode surface limits the reaction process. The reaction process therefore should be described by Fick's diffusion equation, making the output signal proportional to the oxygen content.

Another exemplary embodiment of the invention is a method for sensing oxygen in a sample gas. The method includes controlling a rate of diffusion of oxygen from the sample gas into a sensing chamber; and measuring a current through the sensing electrode that results from a catalyzed reaction of oxygen in the sensing chamber. A bias voltage between the first and second electrodes (e.g., sensing and reference electrodes) that are in electrical contact with a solid electrolyte causes the sensing electrode to capture ions and electrons, which were respectively provided by the counter electrode and the polymer electrolyte. The counter electrode is driven to create the hydrogen ions and electrons from water to supply to sensing electrode. The net reaction is water to water. Accordingly, the sensing method does not consume material in a sensor and can be used in a sensor having a long useful life. The control of the diffusion, which can be implemented using a capillary pore that limits the diffusion rate and the reaction rate so that the measured current is proportional to the chemical content of the gas diffusing into the sensing chamber.

BRIEF DESCRIPTION OF THE DRAWINGS

Use of the same reference symbols in different figures indicates similar or identical items.

DETAILED DESCRIPTION

In accordance with an aspect of the invention, an oxygen sensor uses a solid polymer electrolyte (SPE) and a fuel cell reaction to measure the oxygen concentrations in a sample gas. A SPE oxygen sensor in accordance with an embodiment of the invention avoids electrolyte leakage and has a significantly improved life and response time when compared to the galvanic cell oxygen sensor. The sensor also permits detection and measurement of oxygen at room temperature and has a structure that can be easily miniaturized.

Figure 1:
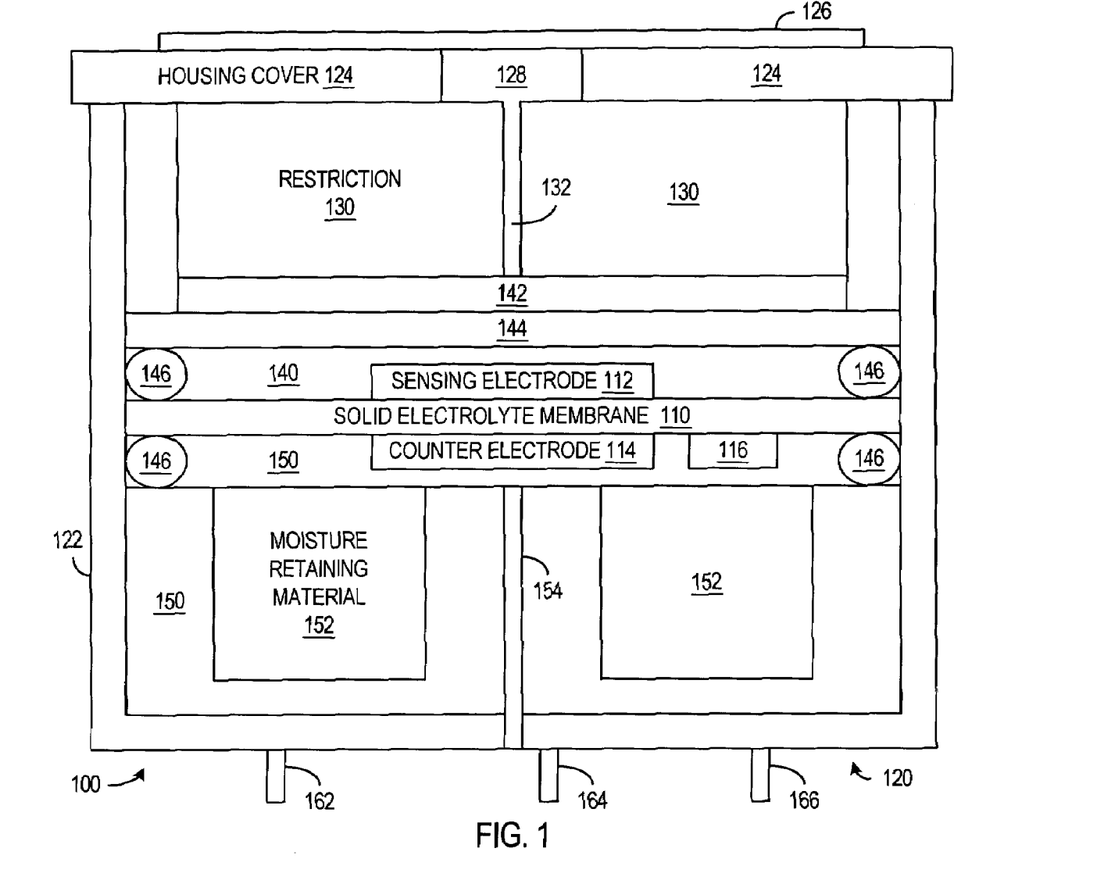
FIG. 1 shows a solid polymer electrolyte (SPE) oxygen sensor in accordance with an embodiment of the invention.

FIG. 1 illustrates an oxygen sensor 100 in accordance with an embodiment of the invention. As illustrated, oxygen sensor 100 includes a solid electrolyte membrane 110 bonded to a sensing electrode 112, a counter electrode 114, and a reference electrode 116. Housing 120, which can be made of a rigid chemically inert material such as Teflon, includes a bottom housing 122 and a cap 124 that enclose solid electrolyte membrane 110 and electrodes 112, 114, and 116.

In sensor 100, an inlet system includes a dust cover 126 on housing cover 124, an inlet hole 128 through housing cover 124, and a diffusion capillary 132 through a restrictor 130. Dust cover 126, which can be made of a material such as polypropylene or polyester, prevents dust and other particulate contaminants from entering sensor 100 and thereby protects electrolyte membrane 110 and sensing electrode 112 from contamination.

Capillary 132 controls the gas diffusion rate to sensing electrode 112. In an exemplary embodiment, capillary 132 is less than about 0.1 µm in diameter and about 0.5 mm long. More generally, the diameter and length of capillary 132 limit the rate of diffusion of oxygen into a sensing chamber 140 and can be adjusted for the specific geometry and reaction rate of sensor 100. An oxygen permeable membrane such as a polytetrafluoroethylene could alternatively be used to control diffusion, but would typically suffer from greater temperature variations. By controlling the diffusion rate, capillary 132 also controls the availability of oxygen at sensing electrode 112, and as described further below, the diffusion rate becomes the limiting factor that controls the reaction rate for the reduction oxygen at sensing electrode 112, the mass transport, and the resulting measurement current.

An oxygen permeable membrane 142 and a glass microfiber paper 144 are between capillary 132 and sensing chamber 140. Membrane 144, which can be made of Teflon or another suitable material, protects capillary 132 from water or other substances from inside sensor 100 that might otherwise block capillary 132. Glass micro-fiber paper 144, which can be treated with sulfuric acid, helps adjust the humidity in sensing chamber 140.

A reservoir 150 containing a moisture-retaining material 152 such as a cotton or glass fiber paper permeated with sulfuric acid, silicon gel, or polymers (e.g., a polyethylene glycol or polypropylene carbonate) are in bottom housing 122. Moisture retaining material 152 releases water as required to maintain a suitable humidity or moisture level in electrolyte membrane 110. O-ring gaskets 146 are above and below solid electrolyte membrane 110 to prevent moisture from reservoir 150 from leaking past membrane 110 and to prevent the gas from entering into sensing chamber 140.

A key part of sensor 100 is the assembly including solid electrolyte membrane 110 and electrodes 112, 114, and 116. Many factors such as the composition and treatment of membrane 110, the interfaces of electrodes 112, 114, and 116 to membrane 110, and the arrangement of electrodes 112, 114, and 116 in sensor 100 influence the performance of the membrane/electrode assembly. In an exemplary embodiment of the invention, solid electrolyte membrane 110 is made of Nafion, which a hydrated copolymer of polytetafluoroethylene and polysulfonyl fluoride vinyl ether containing pendant sulfuric acid groups. Other protonic conductive polymers such as polyethylene glycol, polyethylene oxide, or propylene carbonate could alternatively be used.

A low bulk ionic resistance through membrane 110 is desired for a fast response. An important factor influencing the bulk ionic resistance is the interface resistance between solid electrolyte membrane 110 and electrodes 112, 114, and 116. Accordingly, a good contact between the electrodes and membrane 110 is important, and in accordance with an aspect of the invention, a hot-pressed method is employed to attach electrodes 112, 114, and 116 to membrane 110. In one specific fabrication process, a Nafion membrane, which is about 0.18 mm thick, is coated with liquid Nafion or a Nafion solution. The coated membrane and platinum or noble metal electrodes/catalysts are then heated to about 120° C. while being pressed together at a pressure of about 2000 BL for 20-30 seconds, then moved to ambient air for cooling.

The bulk ionic resistance also depends on the resistance or resistivity of solid electrolyte membrane 110. To lower the resistance of a Nafion membrane, a Nafion membrane can be acid treated before pressing electrodes 112, 114, and 116 on membrane 110. One specific acid treatment applies sulfuric acid ($H_2SO_4$) at a concentration of 0.5 to 1 mol/L to the membrane. However, combining phosphoric acid ($H_3PO_4$) additives with Nafion can improve Nafion's high temperature electrochemical performance. In one specific acid treatment, a Nafion membrane is immersed in concentrated phosphoric acid (85% wt.) and heated to about 150° C. for 1 hour, after the membrane is immersed in boiling water and 3% hydrogen peroxide. The membrane is moved to deionized water for washing off dissociation acid. A report in Mat. Res. Symp. Proc. 1998, vol. 496, p. 217, also describes some treatment processes for Nafion.

Three pins 162, 164, 166 are respectively connected to electrodes 112, 114, and 116 via platinum wires (not shown) inside sensor 100. The wires can be soldered to electrodes 112, 114, and 116 and to pins 162, 164, and 166 using conventional techniques. Pins 162, 164, and 166 thus enable connection of external sensor electronics for current output and bias input.

Figure 2:
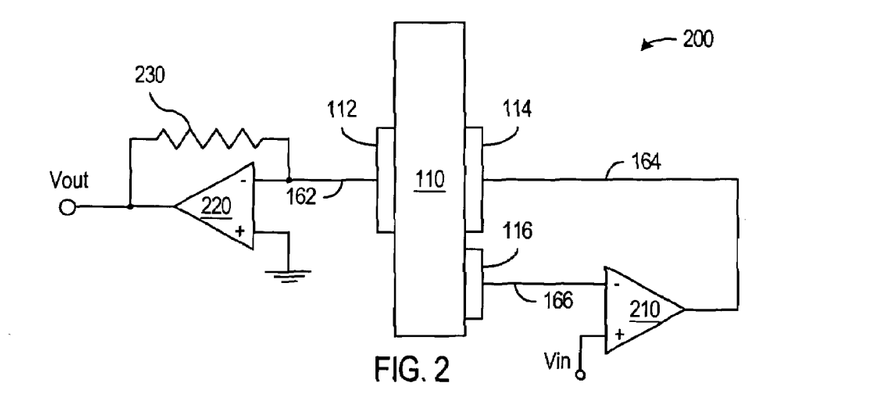
FIG. 2 shows the operating circuit of a three-electrode system sensor for the sensor of FIG. 1.

FIG. 2 is a circuit diagram illustrating the operation of sensor 100 and the connections of pins 162, 164, and 166 to electrodes 112, 114, and 116 in sensor 100 and to electrical components such as differential amplifiers 210 and 220 and a resistor 230 on a printed circuit board. Alternatively, the electrical components illustrated in FIG. 2 could all be integral parts of the oxygen sensor.

During operation, sensing electrode 112 catalyzes a reaction in which the oxygen that enters into sensor 100 and diffuses to sensing electrode 112 captures the electrons and combines with the hydrogen ions from the polymer solid electrolyte 110 to form water as indicated in Equation (1).

$$\tfrac{1}{2}O_2 + 2H^+ + 2e^- \rightarrow H_2O \quad (1)$$

Differential amplifier 210 has input terminals coupled to reference electrode 116 and to a reference voltage Vin and an output terminal coupled to counter electrode 114. Differential amplifier 210 thus drives counter electrode 114 to cause electrolysis of water that creates hydrogen ions and offers electrons to compensate for the hydrogen ions and the electrons consumed at sensing electrode 112 in the reaction of Equation (1). The electrolysis operation is shown in Equation (2).

$$H_2O \rightarrow 2H^+ + \tfrac{1}{2}O_2 + 2e^- \quad (2)$$

The electrons flowing to sensing electrode 112 form an output current that depends on the rate of oxygen consumption, and the output current can be measured to determine the oxygen concentration at sensing electrode 112. The hydrogen ions created at counter electrode 114 flow to sensing electrode through polymer electrolyte 110. The oxygen created at the counter electrode 114 partly diffuses out of sensor 100 through a hole 154 through reservoir 150 and hosing 122 or is kept in the reservoir 150.

The reactions of Equations (1) and (2) balance, so that the overall reaction converts water to water, and oxygen at sensing electrode 112 into oxygen at counter electrode 114. The electrons liberated at counter electrode 114, the electrons captured at sensing electrode 112, and the hydrogen ions migrating from counter electrode 114 to sensing electrode 112 via the solid polymer electrolyte 110 flow at rates that depend on the reaction rate for the reaction of Equation (1). Differential amplifier 220 drives an output voltage Vout to a level such that a current through resistor 230 matches the flow of electrons required for the reaction at sensing electrode 112. Voltage Vout is thus proportional to the reaction current, and the resistance of resistor 230 can be adjusted to control the proportionality constant between voltage Vout and the oxygen concentration.

Figure 3A:
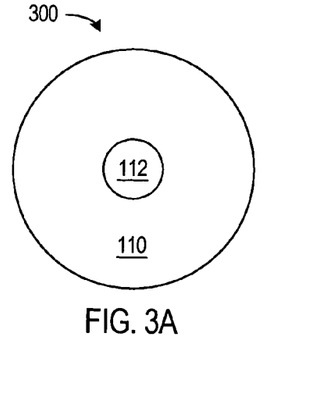
FIGS. 3A, 3B, and 3C respectively show top, bottom, and side views of a solid electrolyte membrane having an electrode pattern in accordance with an embodiment of the invention.
Figure 3B:
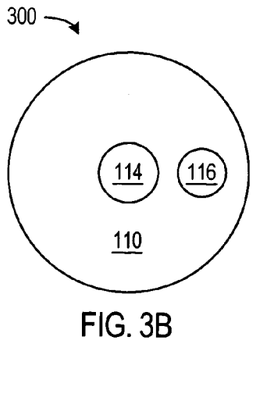
Figure 3C:
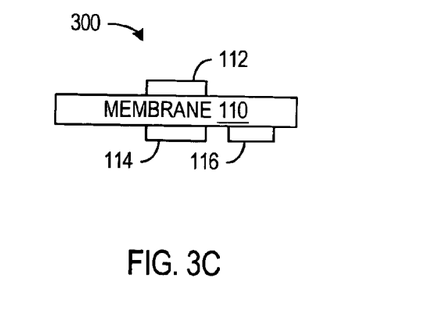

The configuration of terminals 112, 114, and 116 on membrane 110 can control the efficiency of the reduction of oxygen at sensing electrode 112 and therefore the level of the measurement current. FIGS. 3A, 3B, and 3C respectively show top, bottom, and side views of an electrode/membrane assembly 300 in accordance with an embodiment of the invention having sensing electrode 112 on one side of electrolyte membrane 110 and counter and reference electrodes 114 and 116 on the other side of electrolyte membrane 110.

In an exemplary embodiment of the invention, electrolyte membrane 110 is a disk of acid-treated Nafion having a diameter of about 1.5 mm and a thickness between about 0.1 mm and about 0.2 mm. Sensing electrode 112 is preferably made of a catalyst material for the reaction of Equation (1) and can be, for example, platinum, gold, ruthenium, palladium, iridium, platinum/ruthenium, platinum/iridium, platinum/palladium alloy, carbon, or platinum/carbon that is porous and preferably about 0.2 mm thick. Counter electrode 114 and reference electrode 116 can be made of the same material as sensing electrode. Accordingly, reference electrodes can also be made of a noble metal such as platinum or gold or a high conductivity metal salt combination such as silver/silver chloride.

The electrodes are circular in the illustrated embodiment for ease of manufacturing. In the exemplary embodiment of the invention, each of sensing electrode 112 and counter electrode 114 has a diameter of about 0.5-0.8 mm, and reference electrode 116 has a diameter of about 0.3-0.4 mm.

For electrode assembly 300, reference electrode 116 is on the side of membrane 110 opposite to sensing electrode 112 and is relatively isolated from the environment. The reference potential is thus more stable against changes in oxygen concentration in the environment, and also avoids a potential shift that could lead to a measurement error. Counter electrode 114 is also on the side of membrane 110 that is opposite to sensing electrode 112. This prevents the reaction products (e.g., freed oxygen) at counter electrode 114 from interfering with the sensing electrode reaction.

Figure 4A:
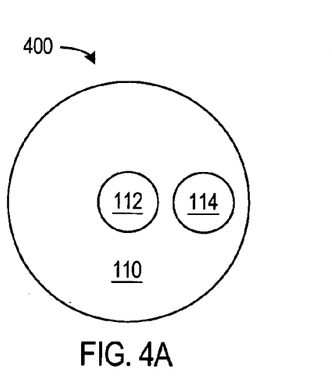
FIGS. 4A, 4B, and 4C respectively show top, bottom, and side views of a solid electrolyte membrane having another electrode pattern in accordance with an embodiment of the invention.
Figure 4B:
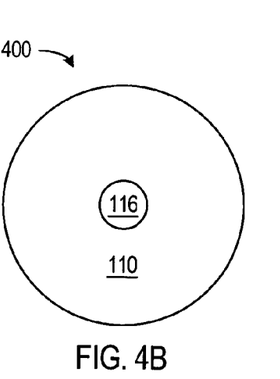
Figure 4C:
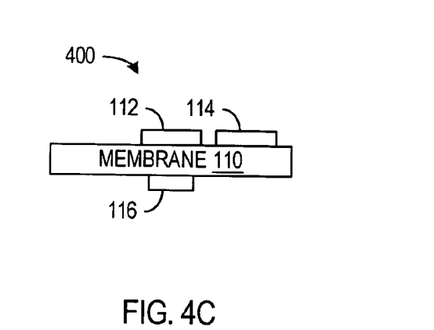

FIGS. 4A, 4B, and 4C respectively show top, bottom, and side views of an electrode/membrane assembly 400 in accordance with an embodiment of the invention having sensing and counter electrodes 112 and 114 on one side of electrolyte membrane 110 and reference electrode 116 on the other side of electrolyte membrane 110. Membrane 110 and electrodes 112, 114, and 116 in assembly 400 can have the same chemical composition and dimensions as corresponding structures in assembly 300 described above.

Electrode/membrane assembly 400, like assembly 300, has the advantage of isolating reference electrode 116 on the opposite side from sensing electrode 112 and thus has good reference voltage stability. Additionally, having counter electrode 114 on the same side as sensing electrode 112 can speed up the rate of mass transport by reducing the distance that hydrogen ions must travel through solid electrolyte membrane 110. With assembly 400, higher sensitivity is expected because of high mass transport rates in the absence of a membrane or significant liquid film barrier. Electrodes 112 and 114 can also share the same sample gas and humidity, giving the two electrodes 112 and 114 the same reaction condition. However, a suitable distance between sensing and counter electrodes should be considered because a short distance can result in the reaction products of counter electrode 114 affecting the reaction at sensing electrode 112.

Figure 5A:
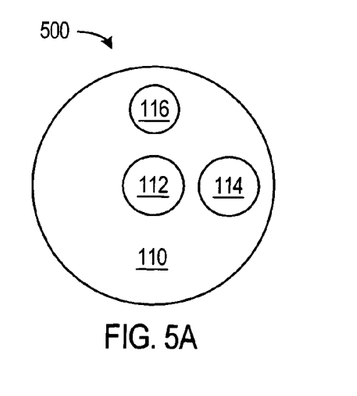
FIGS. 5A and 5B respectively show top and side views of a solid electrolyte membrane in accordance with an embodiment of the invention having three electrodes on the same side of the membrane.
Figure 5B:
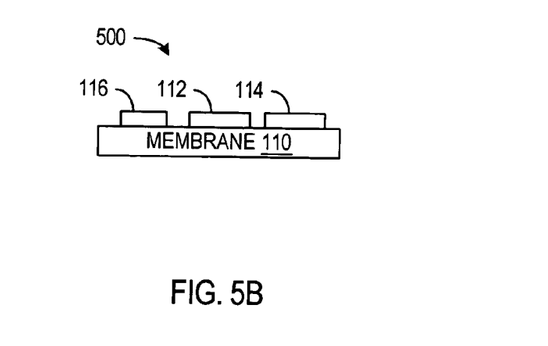

FIGS. 5A and 5B respectively show a top view and a side view of a electrode/membrane assembly 500 in accordance with an embodiment of the invention having electrodes 112, 114, and 116 all on the same side of solid electrolyte membrane 110. This configuration has the advantage of a high mass transport rate and may also simplify the structure of the electrical connections to electrodes 112, 114, and 116.

Figure 6A:
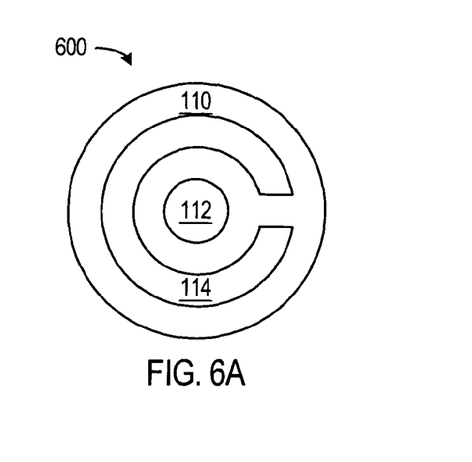
FIGS. 6A and 6B respectively show top and bottom views of a solid electrolyte membrane in accordance with an embodiment of the invention where sensing and counter electrodes are a disk and a surrounding ring.
Figure 6B:
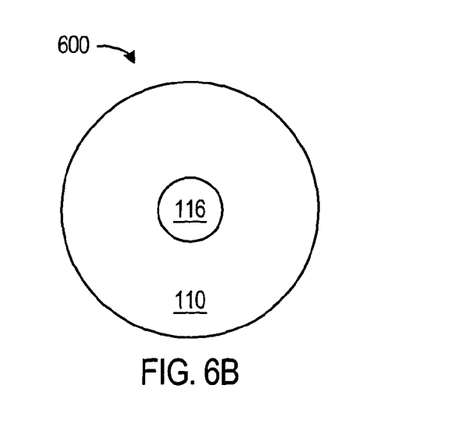

FIGS. 6A and 6B respectively show top and bottom views of an electrode/membrane assembly 600 having a ring-disk type configuration where a ring-shaped counter electrode 114 surrounds a circular sensing electrode 112. The concentric electrode configuration of assembly 600 provides a low ionic bulk resistance between sensing and counter electrodes 112 and 114 and provides a high stability for reference electrode 116.

An exemplary fabrication process for assembly 300, 400, 500, or 600 starts with a Nafion membrane 110 that may be acid treated as described above. Top and/or bottom faces of the Nafion membrane are then coated with liquid Nafion, before a heat-pressure device presses electrodes 112, 114, and 116 on the face or faces of the Nafion membrane to form a three electrode system.

Figure 7:
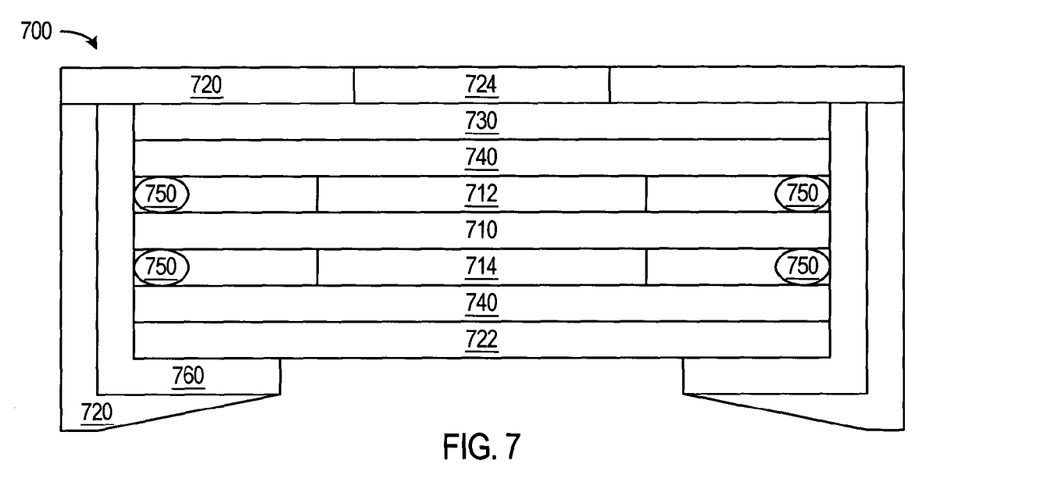
FIG. 7 illustrates a button-type oxygen sensor in accordance with an embodiment of invention.

FIG. 7 shows a button type of oxygen sensor 700 in accordance with an embodiment of invention. Button sensor 700 includes a series of substantially flat elements that can be stacked in contact with each other to provide a very compact sensor configuration. As an electrode system, sensor 700 includes a solid polymer electrolyte membrane 710 bonded to a first electrode 712 and second electrode 714. Each of membrane 710, electrode 712, and electrode 714 can be disk-shape, and electrodes 712 and 714 are generally smaller than membrane 710 to provide spaces for gas around electrodes 712 and 714.

A rigid thin housing made of a metal such as stainless steel includes a lower housing 720 and a cap 722 that enclose the electrode system. A hole 724 in housing 720 and a gas permeable membrane 730 and a paper element 740 inside housing 720 permit gas flow to electrode 712. Gas permeable membrane 730, which can be made of material such as polypropylene and polyester, controls the gas diffusion rate from outside sensor 700 to electrode 712. Paper element 740 can be a glass microfiber paper that is permeated with sulfuric acid (e.g., 6 mol/L $H_2SO_4$) contacts first electrode 712 and serves to adjust reaction humidity. Paper 740 of the same type is also placed on the second electrode 714 as a micro-reservoir to keep humidity in solid polymer electrolyte membrane 710. Rubber O-rings 750 are respectively placed on the two sides of the solid polymer electrolyte membrane 710 to prevent gas or moisture leakage.

Housing 720 and cap 722 can be made of metal or another conductive material to act as electric contacts for supplying a bias voltage and outputting a current signal. Accordingly, housing 720 is electrically connected to electrode 712, and cap 722 is electrically connected to electrode 714. Conductive bands or similar structures (not show) can be used to provide the electrical conductivity through intervening elements such as gas permeable membrane 730 and paper layers 740. An insulation material 760 such as plastic or rubber electrically insulates cap 722 from housing 720.

The basic operating principle of oxygen sensor 700 are the same as for oxygen sensor 100 of FIG. 1, but in sensor 700, second electrode 714 serves as the counter electrode for generation of hydrogen ions and free electrons and as the reference electrode relative to sensing electrode 712. To function as a counter electrode, second electrode 714 is positively biased (e.g., to about 0.6 V) to cause the reaction of Equation (2) that provides electrons to sensing electrode 712 and protons or hydrogen ions to solid polymer electrolyte 710. Sensing electrode 712 can be connected to the input of an amplifier in the same manner as sensing electrode 112 in FIG. 2 so that an output voltage depends on a rate of oxygen reduction reaction at sensing electrode 712.

Gas permeation membrane 730 limits oxygen diffusion to sensing electrode 712, so that the reaction rate and output signal are proportional to the diffusion rate. According to Fick's diffusion equation, the diffusion rate is proportional to the oxygen content outside of gas permeation membrane 730, so that the output signal is proportional to oxygen content.

The button type oxygen sensor 700 can provide a compact sensor configuration. In one exemplary embodiment, sensor 700 has an overall diameter of about 20 mm and a thickness of about 3 mm for a total volume of about 1 $cm^3$.

The sensing processes in sensor 100 and 700 generally include four steps that could potentially limit the overall reaction rate and therefore the measurement signal. The steps are: gas diffusion to sensing electrode surface; the sensing electrode catalytic reaction; transfer of electrons and ions to the sensing electrode; and the removal of electrode reaction products from the electrode surface. The slowest of these steps creates a bottleneck that will control the reaction rate for the whole process. If the whole process is controlled by gas diffusion to the sensing surface, in other words, if the diffusion is the bottleneck, the gas concentration has a linear relation with the reaction rate and the output signal because the Fick's equation indicates that the diffusion is proportional to the oxygen content.

Figure 8:
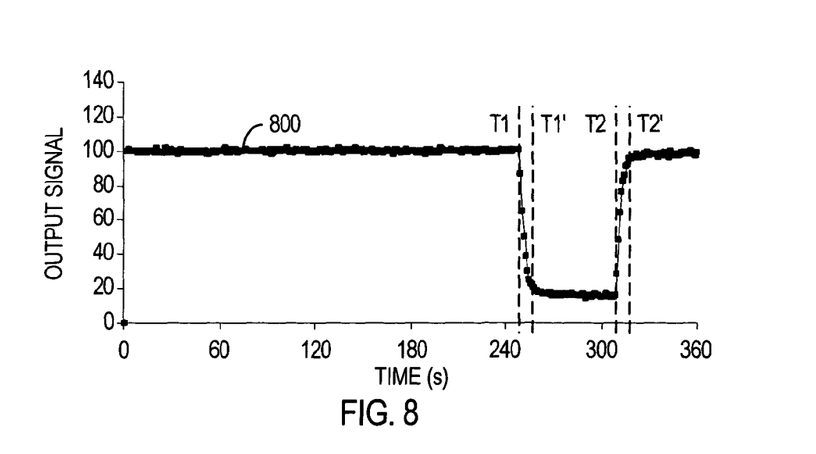
FIG. 8 is a graph showing the response of the sensor of FIG. 1 to different concentrations of oxygen.

FIG. 8 shows a plot 800 of the output signal of a sensor such as illustrated in FIG. 1 or 7. For plot 800, the oxygen concentration remains constant until a time T1 when the oxygen concentration in the target gas suddenly drops. In response, the output signal drops and reaches 90% of the full response at a time T1' that is less than 10 seconds later. Similarly, at time T2, the oxygen concentration returns to the initial level, and the output signal rises to 90% of the full response at a time T2' that is less than 10 seconds later. The fast response time of sensor 100, which is impressively faster than that of currently available commercial oxygen sensors may be attributed to high electrocatalytic activity of sensing electrode 112, and a reaction rate that is diffusion limited. The small volume of sensing chamber 140, which is between sensing electrode 112 and capillary 132 in sensor 100 of FIG. 1, quickly reaches equilibrium where the diffusion rate and sensing reaction rate are the same. In an exemplary embodiment, sensing chamber 140 has a volume less than about 0.01 $mm^2$.

Figure 9:
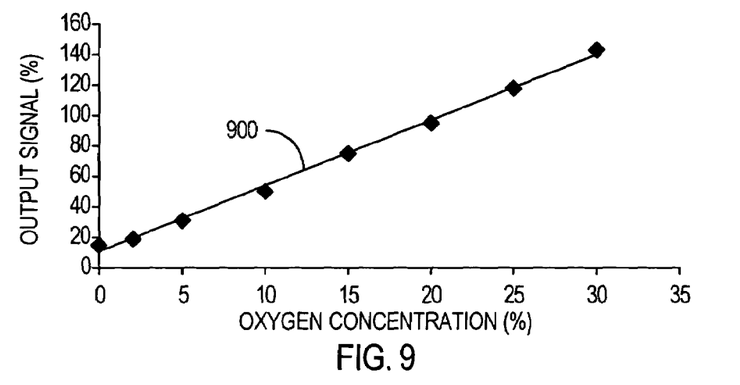
FIG. 9 illustrates the linear response of the sensor of FIG. 1 to oxygen concentration.

FIG. 9 shows a plot 900 of the output signal from sensor 100 as a function of oxygen concentration outside sensor 100. For plot 900, sensing electrode 112 has a fixed potential of about −0.6 V with respect to reference electrode 116. Plot 900 illustrates a suitably linear relationship is obtained for oxygen content in the range of 0 to 30%. The measurement signal of plot 900 shows that the oxygen diffusion rate through capillary 132 is satisfactorily described by Fick's diffusion equation (i.e., is proportional to the oxygen content) over a range of 0-30% oxygen. Accordingly, the reading from sensor 100 represents the percentage of oxygen in the gas sample, and is independent of total gas pressure.

An oxygen content above about 30% oxygen presents additional complications for measurement in sensor 100. In particular, if the oxygen content is above about 30%, the diffusion rate may no longer be proportional to the oxygen content, requiring a non-linear conversion of the output signal to an oxygen content value. Further, if the diffusion rate becomes too high, the reaction rate at sensing electrode 112 becomes the limiting factor of the overall process and the resulting measurement signal, and sensor 100 cannot distinguish higher oxygen content levels.

Figure 10:
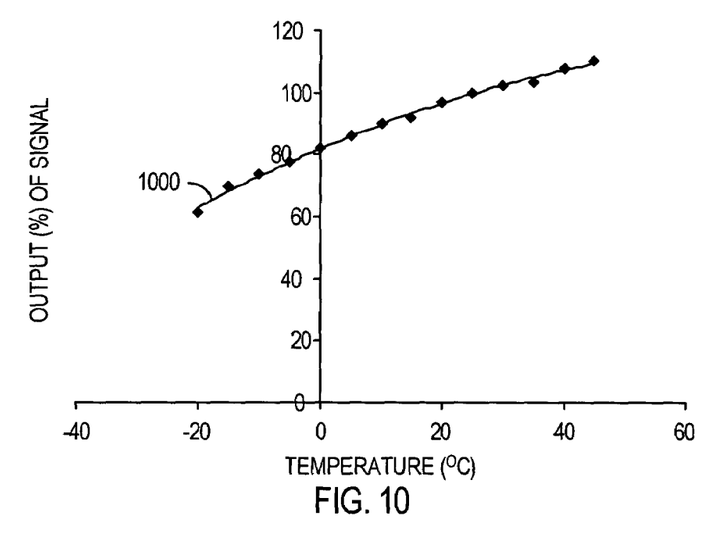
FIG. 10 shows the influence of the ambient temperature on the sensor of FIG. 1 or 7.

FIG. 10 shows a plot 1000 of the measurement signal as a function of temperature for a gas sample containing a fixed oxygen content. The output signal of sensor 100 varies slightly with gradual changes in temperature as shown in FIG. 9. The temperature effect may arise from thermal changes in gas diffusion rates, electrode reaction rates, and membrane resistance. When exposed to a step change in temperature, sensor 100 exhibits a transient response, which is a decrease in the measurement signal for a drop in temperature and an increase in the measurement signal for a rise in temperature.

Figure 11:
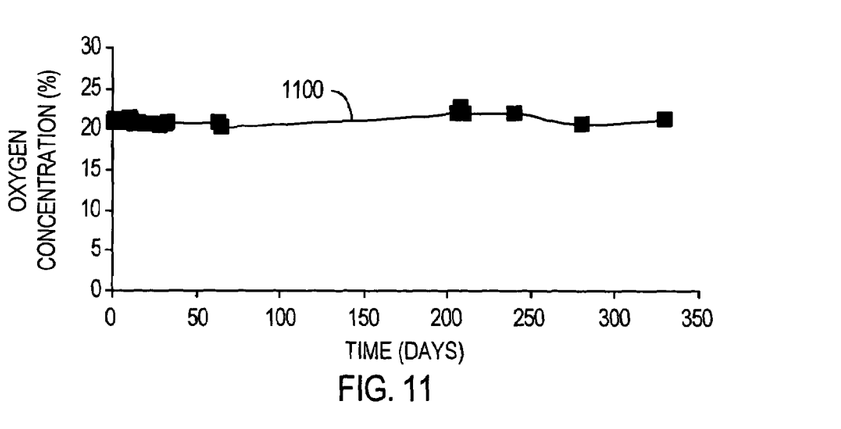
FIG. 11 shows the results of a stability test for the sensor of FIG. 1 or 7.

FIG. 11 shows a plot 1100 illustrating the long-term stability test of the measurement signal from a sensor 100 for a sample gas having a fixed oxygen content, e.g., in ambient air sensed over several months. No large signal change is found after the long time testing. The uniformity of the measurement arises from the ability of sensor 100 to measure oxygen without consuming an electrode or other material. In particular, oxygen is reduced on sensing electrode 112 into water, and that water is consumed to produce hydrogen ions and oxygen at counter electrode 114. The net reaction is no change in the constituents of sensor 100. Therefore, sensor 100 can provide consistent measurements as long as the material and structure in sensor 100 are unchanged.

Although the invention has been described with reference to particular embodiments, the description is only an example of the invention's application and should not be taken as a limitation. Various adaptations and combinations of features of the embodiments disclosed are within the scope of the invention as defined by the following claims.

What is claimed is:

1. A gas sensor comprising
    a block of a solid electrolyte;
    a sensing electrode in electrical contact with the block, wherein the sensing electrode catalyzes a reaction of oxygen with hydrogen ions and electrons to produce water and a current through the sensing electrode caused by the electrons captured indicates a measured oxygen concentration;
    an insert between the sensing electrode and a source of a gas being measured, wherein the insert controls a flow of oxygen to the sensing electrode so that a diffusion rate limits a rate of the reaction at the sensing electrode; and
    a counter electrode in electrical contact with the block, wherein a biasing of the counter electrode breaks down water to produce electrons and hydrogen ions in the block.

2. The gas sensor claim 1, further comprising a reference electrode in electrical contact with the block.

3. The sensor of claim 2, wherein the reference electrode comprises a material selected from a group consisting of platinum and Ag/AgCl.

4. The sensor of claim 1, wherein the insert includes a capillary pore that limits the flow of oxygen.

5. The sensor of claim 4, wherein the capillary pore has a diameter less than 0.1 µm to control oxygen diffusion.

6. The sensor of claim 1, wherein the insert comprises a gas permeable membrane.

7. The sensor of claim 1, further comprising a reservoir adjacent the block, wherein the reservoir contains water that maintains humidity in the block.

8. The sensor of claim 7, further comprising a moisture-retaining agent in the reservoir.

9. The sensor of claim 8, wherein the moisture-retaining agent comprises a polymer material or an acid.

10. The sensor of claim 9, wherein the acid comprises $H_2SO_4$ or $H_3PO_4$.

11. The sensor of claim 1, further comprising a rigid housing that encloses the block.

12. The sensor of claim 1, wherein the solid electrolyte is a protonic conductive electrolyte membrane having a thickness in the range of approximately 0.01 to 0.2 mm.

13. The sensor of claim 12, wherein the solid electrolyte comprises a perfluorinated ion-exchange polymer.

14. The sensor of claim 1, wherein the block comprises a Nafion membrane.

15. The sensor of claim 14, wherein the Nafion membrane is treated with an acid.

16. The sensor of claim 15, wherein the acid is $H_3PO_4$.

17. The sensor of claim 14, wherein the sensing and counter electrodes are hot-pressed on the Nafion membrane.

18. The sensor of claim 1, wherein the sensing electrode comprises a material selected from a group consisting of platinum, gold, ruthenium, palladium, iridium, platinum/ruthenium, platinum/iridium, platinum/palladium alloy, carbon, and platinum/carbon.

19. The sensor of claim 1, wherein the sensing electrode is made of a material that catalyzes oxygen reduction.

20. The sensor of claim 1, wherein the counter electrode comprises a noble metal selected from a group consisting of platinum and gold.

21. The sensor of claim 1, wherein the sensing electrode is on a first surface of the block and the counter electrode is on a second surface of the block.

22. The sensor of claim 21, wherein a reference electrode is on the second surface of the block.

23. The sensor of claim 1, wherein the sensing and counter electrodes are on a first surface of the block.

24. The sensor of claim 23, wherein the sensing electrode is circular, and the counter electrode has a ring shape that surrounds the sensing electrode.

25. The sensor of claim 24, wherein the sensing electrode has a diameter of 0.6 mm, and the counter electrode has a width of 0.2 mm.

26. The sensor of claim 23, wherein a reference electrode is on a second surface of the block.

27. The sensor of claim 23, wherein a reference electrode is on the first surface of the block.

28. The sensor of claim 1, wherein each of the sensing and counter electrodes has a diameter between 0.5 and 0.8 mm.

29. The sensor of claim 1, wherein the biasing of the sensing electrode is between −1.0 to 1.0 voltage.

30. The sensor of claim 1, wherein the overall size of the sensor is less than about 5.0 $cm^3$.

31. The sensor of claim 1, wherein the overall size of the sensor is less than about 1.0 $cm^3$.

32. A gas sensor comprising:
    a block of a solid electrolyte, wherein the block comprises a protonic conductive electrolyte slice including a conducting polymer selected from a group consisting of poly(ethylene glycol), poly(ethylene oxide), and poly(propylene carbonate);
    a sensing electrode in electrical contact with the block; and
    a counter electrode in electrical contact with the block, wherein:
    the sensing electrode catalyzes a reaction of oxygen with hydrogen ions and electrons to produce water;
    a biasing of the counter electrode breaks down water to produce electrons and hydrogen ions in the block; and a current through the sensing electrode caused by the electrons captured indicates a measured oxygen concentration.

33. An oxygen sensor comprising:
a block of a solid electrolyte;
first, second, and third electrodes in electrical contact with the block;
a rigid housing that forms a sensing cavity containing at least one of the first, second, and third electrodes;
a restrictor including a capillary pore that limits diffusion of oxygen into the sensing cavity;
first, second, and third terminals in electrical contact respectively with the first, second, and third electrodes, wherein the first, second, and third terminals are electrically isolated from each other to permit independent biasing of the first, second, and third electrodes; and
an electronic circuit that is connected to the first, second, and third terminals to bias the first, second, and third electrodes and measure a current indicating a target gas.

34. The sensor of claim 33, wherein the rigid housing further comprises a reservoir in communication with the block of solid electrolyte to control water content in the solid electrolyte.

35. A button-type oxygen sensor comprising:
a block of a solid polymer electrolyte;
a first electrode on a first surface of the block;
a second electrode on a second surface of the block; and
a rigid housing including a first portion in electrical contact with the first electrode and a second portion in electrical contact with the second electrode.

36. The sensor of claim 35, further comprising an insert between the block and a hole in the housing, wherein the insert includes a membrane that controls a flow of oxygen to the first electrode from the hole.

37. The sensor of claim 36, wherein the membrane allows gases to permeate to the first electrode and rejects water and dust.

38. The sensor of claim 37, wherein the membrane is made of polypropylene and polyester.

39. The sensor of claim 37, further comprising a moisture-retaining material that is within the housing.

40. The sensor of claim 39, wherein each of the block, the membrane, and the moisture-retaining material is disk-shaped, and elements with the housing form a stack of disk-shaped structures.

41. The sensor of claim 35, further comprising a moisture-retaining material that is within the housing.

42. The sensor of claim 41, wherein the moisture-retaining material comprises a glass fiber paper.

43. The sensor of claim 42, wherein the moisture-retaining material further comprises an acid that absorbs water in wet environment and releases water in dry environment.

44. The sensor of claim 43, wherein the acid is a sulfuric acid.

45. The sensor of claim 35, wherein the solid polymer electrolyte is a protonic conductive electrolyte membrane having a thickness in the range of approximately 0.01 to 0.02 mm.

46. The sensor of claim 45, wherein the solid electrolyte comprises a perfluornated ion-exchange polymer.

47. The sensor of claim 45, wherein the block comprise a Nafion membrane.

48. The sensor of claim 47, wherein the Nafion membrane is treated with 85% H3PO4.

49. The sensor of claim 47, wherein the first and second electrodes are hot-pressed on the Nafion membrane.

50. The sensor of claim 35, wherein the block comprises a protonic conductive electrolyte slice including a conducting polymer.

51. The sensor of claim 35, wherein the first electrode and second electrode comprise a material selected from a group consisting of platinum, gold ruthenium, palladium, iridium/ruthenium, platinum/iridium, platinum/palladium alloy, carbon, and platinum/carbon.

52. The sensor of claim 51, wherein the first and second electrodes have a diameter between 0.5 and 0.8 mm.

53. The sensor of claim 35, wherein a bias −0.6 voltage is applied to first electrode relative to the second electrode.

54. The sensor of claim 35, wherein the overall size of the sensor is less than 1.0 cm$^3$.

* * * * *